United States Patent
Iwama et al.

(10) Patent No.: US 8,491,476 B2
(45) Date of Patent: Jul. 23, 2013

(54) ULTRASOUND IMAGING APPARATUS AND METHOD FOR GENERATING ULTRASOUND IMAGE

(75) Inventors: Nobuyuki Iwama, Nasushiobara (JP); Isao Uchiumi, Nasushiobara (JP); Masaaki Ishitsuka, Nasushiobara (JP); Satoshi Kamiyama, Otawara (JP); Toru Hirano, Otawara (JP); Takeshi Fukasawa, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 581 days.

(21) Appl. No.: 12/557,899

(22) Filed: Sep. 11, 2009

(65) Prior Publication Data

US 2010/0087737 A1    Apr. 8, 2010

(30) Foreign Application Priority Data

Oct. 2, 2008 (JP) .................................. 2008-256984

(51) Int. Cl.
*A61B 5/00* (2006.01)
*A61B 8/00* (2006.01)

(52) U.S. Cl.
USPC ........... 600/437; 600/443; 600/447; 600/459; 73/584

(58) Field of Classification Search
USPC .... 600/437, 443, 447, 459; 330/5.5; 367/168; 73/584

See application file for complete search history.

(56) References Cited

U.S. PATENT DOCUMENTS

| 6,028,484 A | 2/2000 | Cole et al. |
| 6,795,374 B2 * | 9/2004 | Barnes et al. ................. 367/138 |
| 2007/0167814 A1 * | 7/2007 | Wakabayashi et al. ....... 600/459 |

FOREIGN PATENT DOCUMENTS

JP    2000-152930    6/2000

* cited by examiner

*Primary Examiner* — Unsu Jung
*Assistant Examiner* — Phong K Huynh
(74) *Attorney, Agent, or Firm* — Oblon, Spivak, McClelland, Maier & Neustadt, L.L.P.

(57) ABSTRACT

A bias gate part supplies a bias current to a transmission pulse generator. The transmission pulse generator receives the supply of the bias current, amplifies an input voltage, and supplies an output voltage obtained by the amplification to array transducer elements. In accordance with the timing of transmitting ultrasound waves from the array transducer elements and the level of the output voltage supplied to the array transducer elements, the bias gate part supplies the bias current to the transmission pulse generator while changing the timing of supplying the bias current.

10 Claims, 6 Drawing Sheets

PRIOR ART

PRIOR ART

ULTRASOUND IMAGING APPARATUS AND METHOD FOR GENERATING ULTRASOUND IMAGE

BACKGROUND OF THE INVENTION

1. Field of the Invention

The present invention relates to an ultrasound imaging apparatus that transmits ultrasound waves to a subject and generates an ultrasound image based on the waves reflected from the subject, more specifically, relates to a transmission system that transmits ultrasound waves.

Moreover, the present invention relates to a method for generating an ultrasound image.

2. Description of the Related Art

For an ultrasound imaging apparatus, an ultrasound transmission/reception circuit has been developed for the purpose of increasing the resolution and sensitivity of an ultrasound image. An arbitrary waveform transmission circuit that is capable of transmitting various waves in accordance with imaging modes has been developed, which is capable of not only transmitting rectangular pulse waves but also transmitting sine waves subjected to Gaussian amplitude modulation so that second harmonic waves are suppressed, transmitting multi-frequency waves in which a plurality of frequencies are combined, and transmitting chirp waves.

As a conventional technique, an ultrasound imaging apparatus provided with a linear amplifier is proposed (e.g., Japanese Unexamined Patent Publication No. 2000-152930). A linear amplifier is capable of securing linearity and operating at high speeds when a bias current is made to flow. An arbitrary waveform transmission circuit of a conventional technique will be described with reference to FIG. 1. FIG. 1 is a block diagram showing a transmission circuit.

The transmission circuit shown in FIG. 1 configures a complementary amplifier. This transmission circuit reversely operates.

When an input voltage Vin is inputted, positive and negative signals are transmitted from input-stage transistors M1 and M2, respectively, and amplified in amplifier-stage transistors M5 to M8 via bias gate transistors M3 and M4. The amplified signals are supplied to array transducer elements 2 from buffer-stage transistors M9 and M10.

Further, this transmission circuit is provided with a part for controlling a bias current. By operating with two power sources VP and VN, this transmission circuit is also provided with two types of bias control power sources. To the gates of the bias gate transistors M3 and M4, control power sources CS1 and CS2 that generate voltages VG1 and VG2, respectively, are connected.

The voltages VG1 and VG2 are controlled so that a bias current flows during a waveform transmission period (a time when a waveform is outputted and predetermined times before and after the time). Since this transmission circuit is bipolar, the bias gate transistor M3 is n-channel and the bias gate transistor M4 is p-channel. Moreover, as the voltages VG1 and VG2, opposite voltages are given.

The operation sequence of the abovementioned transmission circuit is shown in FIG. 2. FIG. 2 is a timing chart showing the operation sequence of the transmission circuit of the conventional technique. The timing chart of FIG. 2 shows the generation voltage waveforms of the control power sources CS1 and CS2 and the waveforms of the bias current, the input voltage Vin and an output voltage Vout. In the abovementioned transmission circuit, the voltages VG1 and VG2 of the control power sources CS1 and CS2 are switched between High and Low so that the bias current flows only when a transmission signal is outputted. Thus, the bias current does not flow when a transmission signal is not outputted.

To be specific, the voltages VG1 and VG2 of the control power sources CS1 and CS2 are switched between High and Low so that supply of the bias current is started a predetermined time before a transmission signal is outputted. Then, the voltages VG1 and VG2 of the control power sources CS1 and CS2 are switched between High and Low so that the supply of the bias current is halted after a lapse of a predetermined time after an arbitrary waveform is transmitted.

This transmission circuit is brought into the active state when a bias current is supplied, thereby being capable of amplifying an input signal. However, in a case that an electric current continuously flows at all times, the power consumption of the transmission circuit increases, and therefore, the temperature of the circuit increases. The ultrasound imaging apparatus executes pulse transmission of ultrasound waves to a living body at predetermined time intervals and thereby receives the waves reflected from an arbitrary depth. Since the transmission circuit is in the halted state except a time when a transmission signal is outputted, the operation of the transmission circuit is halted by halting the supply of the bias current. Thus, increase of the power consumption of the transmission circuit is suppressed, and consequently, it is possible to suppress increase of the temperature of the transmission circuit.

However, in the abovementioned transmission circuit, the bias current is radically turned on/off. Therefore, as shown in FIG. 3, glitch noise is generated when the bias current is turned on/off. The apparatus normally operates to detect the waves reflected from the structure of a living body of the transmission pulses. However, as shown in FIG. 3, different transmission pulses (glitch noise) exist before or after the transmission waveform, and therefore, an ultrasound image may be duplicated. Moreover, there is the fear that the frequency of a transmission band different from a transmission band to image may be detected and consequently resolution may decrease.

In particular, in a case that a transmission waveform is outputted at a low transmission voltage, for example, in the contrast imaging mode of administering an ultrasound contrast agent into the vessel and imaging without destroying the ultrasound contrast agent, glitch noise may reach a voltage level that cannot be ignored with respect to the transmission voltage. In this case, there is a problem that the glitch noise conspicuously appears as an artifact in an ultrasound image. For example, in a case that the voltage of a transmission signal is about several volts, glitch noise reaches a voltage level that cannot be ignored with respect to the transmission signal.

SUMMARY OF THE INVENTION

An object of the present invention is to provide an ultrasound imaging apparatus that is capable of decreasing the influence of noise resulting from turning on/off a bias current for amplifying a transmission signal and thereby decreasing the influence of an artifact, and also provide a method for generating an ultrasound image.

A first aspect of the present invention is an ultrasound imaging apparatus that has: a plurality of transducers; a part configured to receive a synchronizing signal indicating a period for transmitting and receiving ultrasound waves and output a transmission signal after a first time t1 from a time indicated by the synchronizing signal; a bias current supply part configured to receive the synchronizing signal and, in a case that an output voltage supplied to the plurality of transducers is equal to or more than a threshold value, supply a bias current during a time interval ΔT2 including a time interval ΔT1 during which the transmission signal is outputted, before a time point that the first time t1 elapses and after a lapse of a second time t2 shorter than the first time t1 from the time indicated by the synchronizing signal and, in a case that the output voltage is less than the threshold value, keep supplying a bias current from a time point a third time t3 before the time indicated by the synchronizing signal; an amplifier configured to receive the supply of the bias current to amplify the transmission signal to the output voltage and supply the transmission signal to the plurality of transducers; and an image generator configured to generate ultrasound image data based on reception signals received by the plurality of transducers.

According to the first aspect, by controlling the timing of supplying a bias current and the timing of halting the supply in accordance with the level of an output voltage, it is possible to decrease the influence of noise resulting from turning on/off the bias current and decrease the influence of an artifact. For example, by keeping supplying a bias current when the output voltage is less than a threshold value, it is possible to inhibit generation of the noise resulting from turning on/off the bias current. Consequently, even when outputting a low-voltage signal susceptible to the noise, it is possible to inhibit generation of the noise and generate an ultrasound image in which generation of an artifact is suppressed.

Further, a second aspect of the present invention is a method for generating an ultrasound image that includes: receiving a synchronizing signal indicating a period for transmitting and receiving ultrasound waves, and outputting a transmission signal after a time t1 from a time indicated by the synchronizing signal; receiving the synchronizing signal and, in a case that an output voltage supplied to a plurality of transducers is equal to or more than a threshold value, supplying a bias current during a time interval ΔT2 including a time interval ΔT1 during which the transmission signal is outputted, before a time point that the first time t1 elapses and after a lapse of a second time t2 shorter than the first time t1 from the time indicated by the synchronizing signal and, in a case that the output voltage is less than the threshold value, keeping supplying a bias current from a time point a third time t3 before the time indicated by the synchronizing signal; receiving the supply of the bias current to amplify the transmission signal to the output voltage and supply the transmission signal to the plurality of transducers; and generating ultrasound image data based on reception signals received by the plurality of transducers.

DETAILED DESCRIPTION OF THE EMBODIMENTS

Figure 4:
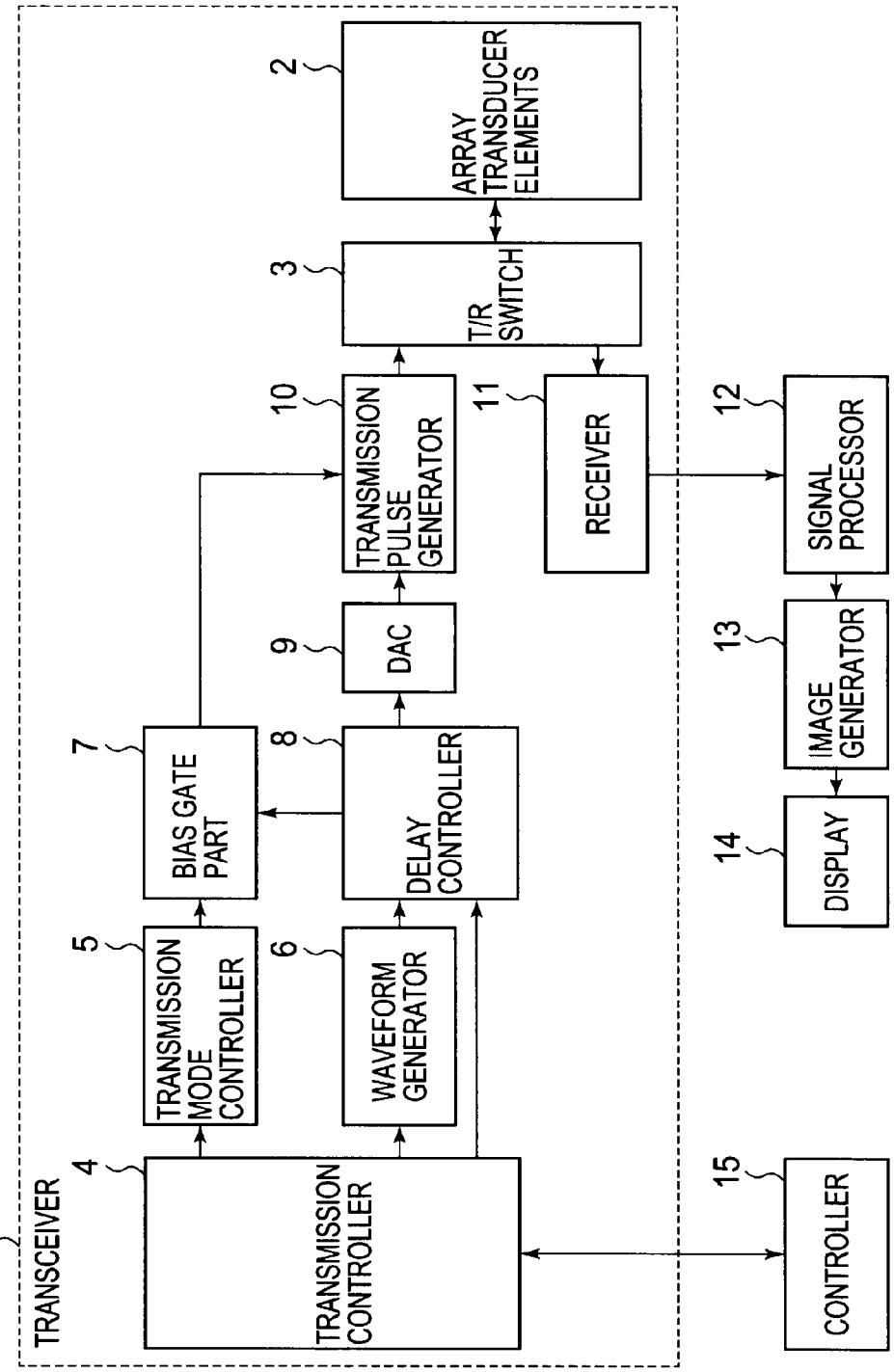
FIG. 4 is a block diagram showing an ultrasound imaging apparatus according to an embodiment of the present invention.

An ultrasound imaging apparatus according to an embodiment of the present invention will be described with reference to FIG. 4. FIG. 4 is a block diagram showing the ultrasound imaging apparatus according to the embodiment of the present invention.

The ultrasound imaging apparatus according to this embodiment includes a transceiver 1, a signal processor 12, an image generator 13, a display 14, and a controller 15.
(Transceiver 1)
The transceiver 1 includes array transducer elements 2, a T/R switch 3, a transmission controller 4, a transmission mode controller 5, a waveform generator 6, a bias gate part 7, a delay controller 8, a DAC (Digital to Analog Converter) 9, a transmission pulse generator 10, and a receiver 11.
(Array Transducer Elements 2)
The array transducer elements 2 include a plurality of ultrasound transducer elements placed in line in a predetermined direction (in the scan direction). Alternatively, the array transducer elements 2 including a plurality of ultrasound transducers placed two-dimensionally may be installed in the ultrasound imaging apparatus. The array transducer elements 2 are connected to the receiver 11 and the transmission pulse generator 10 via the T/R switch 3 that switches transmission of ultrasound waves and reception thereof. In accordance with the number of the ultrasound transducer elements, a plural-channel transmission circuit and a plural-channel reception circuit are installed. The number of the channels is, for example, 64 ch, 128 ch, or 256 ch. The array transducer elements 2 receive supply of the output voltage of a transmission signal from the transmission pulse generator 10 and transmit ultrasound waves to the subject. Then, the array transducer elements 2 receive the waves reflected from the subject and output the received signals to the receiver 11 via the T/R switch 3.
(Transmission Controller 4)
The transmission controller 4 receives transmission parameters supplied from the controller 15 and outputs the transmission parameters to the transmission mode controller 5, the waveform generator 6, and the delay controller 8. The transmission parameters include information of a transmission signal of required ultrasound waves, information representing a period of transmission and reception of the ultrasound waves (a synchronizing signal), information representing the timing of outputting the transmission signal (a first time t1), information representing a time interval ΔT1 of outputting the transmission signal, information representing the timing of supplying a bias current (a second time t2, a third time t3), information of a time interval ΔT2 of supplying a bias current, and information representing a delay time in each of the transmission channels. The information of the transmission signal includes information representing the frequency and amplitude of the transmission signal.

The controller 15 outputs the transmission parameters, which are different for each imaging mode, to the transmission controller 4. For example, in the contrast imaging mode using an ultrasound contrast agent, the voltage of the transmission signal is set to a low voltage. In the contrast imaging mode, the controller 15 outputs the transmission parameters for the contrast imaging mode to the transmission controller 4. In another imaging mode, the controller 15 transmits a high-voltage transmission signal and, in the next transmission and reception, transmits a low-voltage transmission signal. In this imaging mode, the controller 15 outputs the transmission parameters for this imaging mode to the transmission controller 4. For example, transmission parameters that are different for each imaging mode are previously set in the controller 15. Upon selection of an imaging mode by the operator using an input part (now shown), the controller 15 outputs transmission parameters for the imaging mode selected by the operator to the transmission controller 4.

Thus, the ultrasound imaging apparatus according to this embodiment is capable of transmitting and receiving ultrasound waves corresponding to a plurality of modes in accordance with the purposes of diagnoses. For example, the ultrasound imaging apparatus transmits a transmission signal of comparatively high voltage in a normal imaging mode, whereas transmits a transmission signal of comparatively low voltage in the contrast imaging mode using an ultrasound contrast agent.

(Transmission Mode Controller 5)

The transmission mode controller 5 determines the value of a bias current supplied to the transmission pulse generator 10 based on the transmission signal included in the transmission parameters supplied from the transmission controller 4. For example, the transmission mode controller 5 determines the value of the bias current based on the frequency of the transmission signal. Alternatively, the transmission mode controller 5 determines the value of the bias current based on the amplitude of the transmission signal. The transmission mode controller 5 outputs the value of the bias current to the bias gate part 7.

(Waveform Generator 6)

The waveform generator 6 generates transmission waveform data based on the transmission signal included in the transmission parameters supplied from the transmission controller 4 and outputs the transmission waveform data to the delay controller 8.

(Delay Controller 8)

In accordance with the information representing the timing of outputting the transmission signal included in the transmission parameters, the delay controller 8 outputs the transmission waveform data generated by the waveform generator 6 to the DAC 9 at the timing of outputting the transmission signal. The timing of outputting the transmission signal is controlled by the synchronizing signal included in the transmission parameters. The delay controller 8 has a timer for measuring time and outputs the transmission waveform data to the DAC 9 after a lapse of a predetermined time (after the first time t1) from a time indicated by the synchronizing signal.

When a site located deep from the body surface of the subject is to be imaged, the delay controller 8 controls an interval of transmission of ultrasound waves by the synchronizing signal so that the transmission interval becomes long because it takes a long time before the reflection echoes return to the array transducer elements 2. On the other hand, when a site located on the body surface of the subject is to be imaged, the delay controller 8 controls an interval of transmission of ultrasound waves by the synchronizing signal so that the transmission interval becomes short because it takes a short time before the reflection echoes return to the array transducer elements 2.

Further, in accordance with the information representing the timing of outputting the transmission signal (the synchronizing signal) and the information of the transmission signal, the delay controller 8 controls the timing of supplying a bias current for amplifying the transmission signal and the length of a time to supply the bias current.

The supply of the bias current and the halt of the supply are executed by switching on/off a bias gate by the bias gate part 7 described later. In accordance with the information representing the timing of outputting the transmission signal and the information of the transmission signal, the delay controller 8 determines the length of a time to turn on the bias gate, the length of a time to turn off the bias gate, and the timing of switching on/off the bias gate, and gives an instruction to switch on/off the bias gate to the bias gate part 7. That is to say, the delay controller 8 determines the length of a time to flow a bias current, the length of a time not to flow a bias current, and the timing of switching on/off a bias current, and gives an instruction to switch on/off to the bias gate part 7. To be specific, the delay controller 8 determines the timing to switch on/off the bias gate, depending on the information representing the timing of outputting the transmission signal and the voltage level of the transmission signal.

For example, when a high-voltage transmission signal is to be outputted, the delay controller 8 gives an instruction to turn on the bias gate to the bias gate part 7 so that the bias gate is turned on to flow a bias current, at a time point that the second time t2 shorter than the first time t1 elapses (the timing of supplying a bias current) after the time indicated by the synchronizing signal representing the timing of outputting the transmission signal and before a time point that the first time t1 elapses (the timing of outputting the transmission signal). To be specific, the delay controller 8 gives an instruction to turn on the bias gate to the bias gate part 7 so that the bias gate is turned on to flow a bias current, during the time interval ΔT2 including the time interval ΔT1 of outputting the transmission signal after a lapse of the second time t2 from the time indicated by the synchronizing signal. Then, after a lapse of the time interval ΔT2, the delay controller 8 gives an instruction to turn off the bias gate to the bias gate part 7 so that the bias gate is turned off not to flow a bias current.

On the other hand, when a low-voltage transmission signal is to be outputted, the delay controller 8 gives an instruction to turn on the bias gate to the bias gate part 7 so that the bias gate is turned on to flow a bias current, the third time t3 before the time indicated by the synchronizing signal representing the timing of outputting the transmission signal. To be specific, the delay controller 8 gives an instruction to turn on the bias gate to the bias gate part 7 so that the bias gate is turned on to flow a bias current, right before the time indicated by the synchronizing signal. When a low-voltage transmission signal is outputted, the bias gate is left on until the next transmission timing after the transmission signal is outputted. That is to say, the delay controller 8 does not give an instruction to turn off the bias gate to the bias gate part 7, and the bias gate part 7 keeps supplying a bias current to the transmission pulse generator 10.

For example, a threshold value of the voltage is previously set in the delay controller 8. When the voltage of the transmission signal is equal to or more than the threshold value, the delay controller 8 determines that a high-voltage transmission signal is to be transmitted, turns on the bias gate right before the transmission signal is actually transmitted, and turns off the bias gate after the transmission signal is outputted. On the other hand, when the voltage of the transmission signal is less than the threshold value, the delay controller 8 determines that a low-voltage transmission signal is to be transmitted, turns on the bias gate right before the time indicated by the synchronizing signal, and keeps the bias gate on.

For instance, when the voltage of the transmission signal is 100V, the delay controller 8 determines that a high-voltage transmission signal is to be transmitted, turns on the bias gate right before the transmission signal is actually transmitted, and turns off the bias gate after the transmission signal is outputted. On the other hand, when the voltage of the transmission signal is 5V, the delay controller 8 determines that a low-voltage transmission signal is to be transmitted, turns on the bias gate right before the time indicated by the synchronizing signal, and keeps the bias gate on.

(Bias Gate Part 7)

In accordance with the timing of turning on/off the bias gate given by the delay controller 8, the bias gate part 7 supplies a bias current with the value determined by the transmission mode controller 5 to the transmission pulse generator 10. The bias gate part 7 is equivalent to one example of the "bias current supply part" of the present invention.

(DAC 9)

The DAC 9 receives the transmission waveform data from the delay controller 8, converts the transmission waveform data from a digital waveform signal to an analog waveform signal, and outputs the signal to the transmission pulse generator 10.

(Transmission Pulse Generator 10)

The transmission pulse generator 10 receives supply of the bias current from the bias gate part 7 and amplifies the voltage (the input voltage Vin) of the transmission signal supplied from the DAC 9. Then, the transmission pulse generator 10 supplies the output voltage Vout of the transmission signal obtained by the amplification to the array transducer elements 2 via the T/R switch 3. The transmission pulse generator 10 is equivalent to one example of the "amplifier" of the present invention.

A specific example of the bias gate part 7 and the transmission pulse generator 10 will be described. The bias gate part 7 and the transmission pulse generator 10 are configured by, for instance, the transmission circuit shown in FIG. 1. In the transmission circuit shown in FIG. 1, the bias gate part 7 is configured by the control power source CS1, the control power source CS2, the bias gate transistor M3, and the bias gate transistor M4. By this configuration, the bias gate is switched on/off, and a bias current flows to the transmission pulse generator 10. The transmission pulse generator 10 is configured by the bias gate transistors M5 to M8. By this configuration, the input voltage Vin of the transmission signal is amplified, and the output voltage Vout is thereby generated.

For example, when a high-voltage transmission signal is to be outputted, the delay controller 8 gives an instruction to turn on the bias gate to the bias gate part 7 so that supply of a bias current is started right before the transmission signal is outputted. The bias gate part 7 receives the instruction from the delay controller 8 and switches the voltages VG1 and VG2 of the control power sources CS1 and CS2 between High and Low so that the bias current is supplied. After the transmission signal is outputted, the delay controller 8 gives an instruction to turn off the bias gate to the bias gate part 7 so that the supply of the bias current is halted. The bias gate part 7 receives the instruction from the delay controller 8 and switches the power sources VG1 and VG2 of the control power sources CS1 and CS2 between High and Low so that the supply of the bias current is halted.

On the other hand, when a low-voltage transmission signal is to be outputted, the delay controller 8 gives an instruction to turn on the bias gate to the bias gate part 7 so that a bias current is supplied right before the time indicated by the synchronizing signal representing the timing of outputting the transmission signal. The bias gate part 7 receives the instruction from the delay controller 8 and switches the voltages VG1 and VG2 of the control power sources CS1 and CS2 between High and Low so that the bias current is supplied. After the transmission signal is outputted, the delay controller 8 keeps the status of the voltages VG1 and VG2 so that the bias current is supplied until the next transmission timing. Consequently, the bias gate part 7 keeps supplying the bias current to the transmission pulse generator 10. That is to say, the delay controller 8 does not give an instruction to turn off the bias gate to the bias gate part 7, and the bias gate part 7 keeps supplying the bias current to the transmission pulse generator 10.

(Receiver 11)

The receiver 11 includes a preamplifier, an A/D convertor, a reception delay part, and an adder, which are not shown in the drawings.

The preamplifier amplifies echo signals outputted from the respective transducers of the array transducer elements 2 for each of the reception channels. The A/D convertor converts the amplified echo signals from analog to digital. The reception delay part gives a delay time necessary for determining the reception directionality to each of the echo signals having been subjected to the A/D conversion. The adder adds up the echo signals, to each of which the delay time has been given.

By this addition, reflection components from a direction corresponding to the reception directionality are emphasized.

(Signal Processor 12)

The signal processor 12 includes a B-mode processor, a Doppler processor, and a color imaging mode processor. Data outputted from the receiver 11 is subjected to processing in one of the processors. The B-mode processor visualizes amplification information of the echoes and generates B-mode ultrasound data from the echo signals. The Doppler processor derives Doppler shift frequency components and executes the FFT (Fast Fourier Transform) process, etc, to generate data having blood-flow information. The color imaging mode processor visualizes the moving blood-flow information to generate color ultrasound data. The blood-flow information includes information such as the speed, dispersion, and power. The blood-flow information is obtained as binary information.

(Image Generator 13)

The image generator 13 converts the data having been subjected to the signal processing to coordinate data based on the spatial coordinate system (digital scan conversion). For example, the image generator 13 executes scan conversion on the data having been subjected to the signal processing outputted from the B-mode processor, thereby generating B-mode image data representing the shape of the tissue in the subject body. The image generator 13 outputs ultrasound image data such as B-mode image data to the display 14. The display 14 displays an image based on the ultrasound image data such as the B-mode image data.

Figure 5:
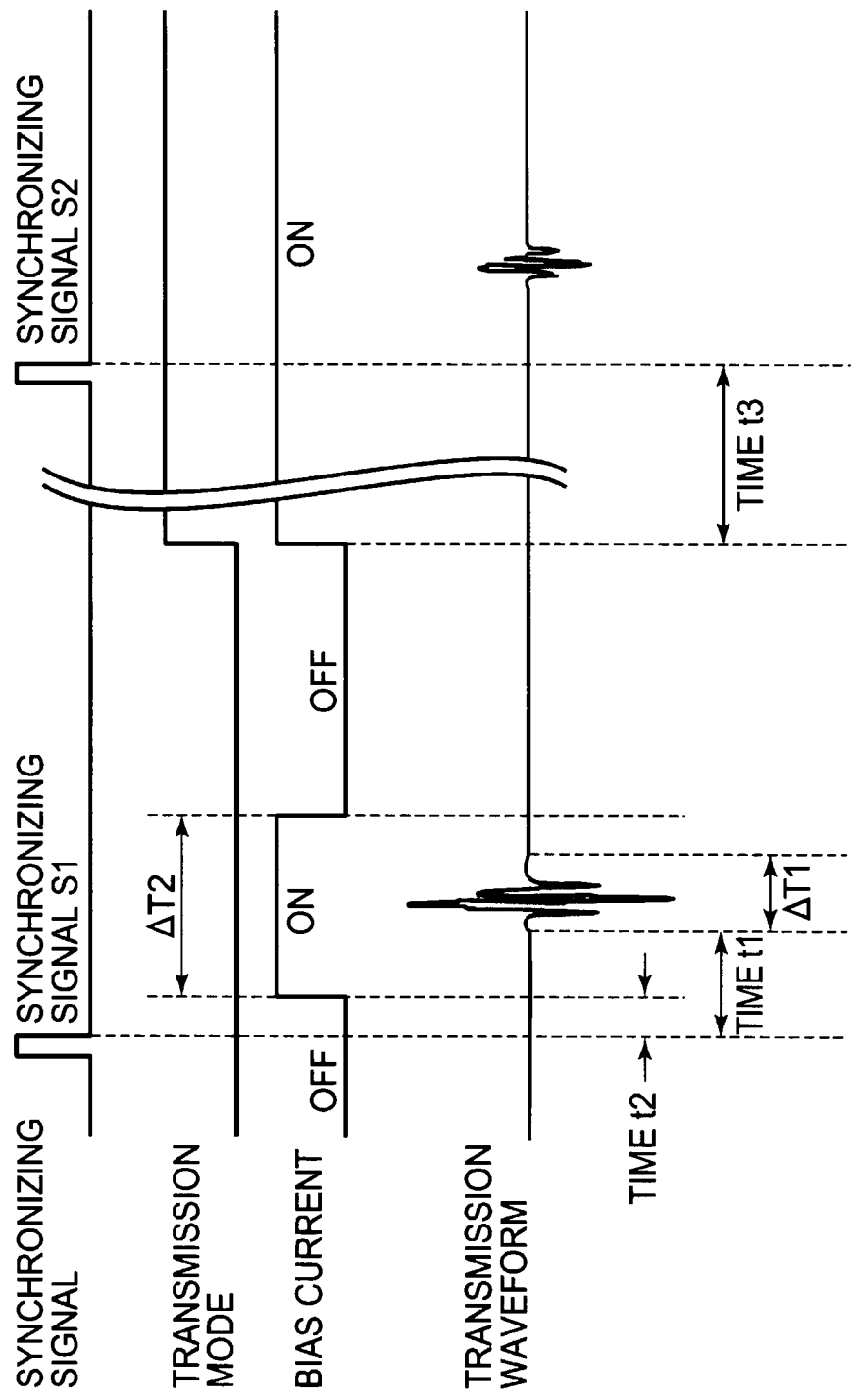
FIG. 5 is a timing chart for describing control of turning on/off a bias current according to the embodiment of the present invention.

Next, control of turning on/off a bias current will be described with reference to FIG. 5. FIG. 5 is a timing chart for describing the control of turning on/off a bias current according to this embodiment of the present invention.

Now, a case of generating and outputting a transmission signal of high voltage, e.g., 100V in response to a synchronizing signal S1 and, after the synchronizing signal S1, generating and outputting a transmission signal of low voltage, e.g., 5V in response to a synchronizing signal S2 will be described.

When a high-voltage transmission signal corresponding to the synchronizing signal S1 is to be outputted, the delay controller 8 gives an instruction to turn on the bias gate to the bias gate part 7 so that a bias current is supplied at a time point that the second time t2 shorter than the first time t1 elapses (the timing of supplying the bias current) after the time indicated by the synchronizing signal S1 and before a time point that the first time t1 elapses (the timing of outputting the transmission signal). Moreover, the delay controller 8 outputs transmission waveform data to the DAC 9 after a lapse of the first time t1 from the time indicated by the synchronizing signal S1. The DAC 9 converts the transmission waveform data from a digital waveform signal to an analog waveform signal and outputs the signal to the transmission pulse generator 10. The bias gate part 7 supplies a bias current to the transmission pulse generator 10 in accordance with the instruction given by the delay controller 8. The transmission pulse generator 10 receives the supply of the bias current from the bias gate part 7 and amplifies the voltage (the input voltage Vin) of the transmission signal supplied from the DAC 9, thereby generating a transmission signal having the output voltage Vout. Then, the transmission voltage having the output voltage Vout is supplied to the array transducer elements 2 via the T/R switch 3.

When the high-voltage transmission signal is outputted, the delay controller 8 gives an instruction to turn off the bias gate to the bias gate part 7 so that the supply of the bias current is halted. To be specific, after a lapse of the predetermined time interval ΔT2 from the second time t2, the delay controller 8 gives an instruction to turn off the bias gate to the bias gate part 7. The bias gate part 7 halts the supply of the bias current in accordance with the instruction given by the delay controller 8. Consequently, the bias current is no longer supplied to the transmission pulse generator 10.

When a low-voltage transmission waveform corresponding to the synchronizing signal S2 is to be outputted after the synchronizing signal S1, the delay controller 8 gives an instruction to turn on the bias gate to the bias gate part 7 so that a bias current is supplied at a time point the third time t3 before the time indicated by the synchronizing signal S2.

Moreover, the delay controller 8 outputs transmission waveform data to the DAC 9 after a lapse of the first time t1 from the time indicated by the synchronizing signal S2. The DAC 9 converts the transmission waveform data from a digital waveform signal to an analog waveform signal and outputs the signal to the transmission pulse generator 10. The bias gate part 7 supplies a bias current to the transmission pulse generator 10 in accordance with the instruction given by the delay controller 8. For example, at a time point that the reception ends in the transmission and reception of ultrasound waves corresponding to the synchronizing signal S1 (a time point the third time t3 before the time indicated by the synchronizing signal S2), the delay controller 8 gives an instruction to turn on the bias gate to the bias gate part 7. When a low-voltage transmission signal is to be outputted, the delay controller 8 does not give an instruction to turn off the bias gate to the bias gate part 7 after the transmission signal is outputted. Consequently, the bias gate part 7 keeps supplying the bias current to the transmission pulse generator 10. When a low-voltage transmission signal is outputted continuously after the synchronizing signal S2, the bias gate is not turned off. Therefore, the supply of the bias current is continued and no glitch noise is generated during this period.

As described above, in the case of outputting a high-voltage transmission signal, it is possible, by supplying a bias current only during the time interval ΔT2 including the time interval ΔT1 during which the transmission signal is outputted, and halting the supply of the bias current during the rest of the time, to inhibit increase of the power consumption of the transmission circuit. Turning on/off the bias current in times before and after the output of the transmission signal generates glitch noise before and after the transmission signal. However, since the voltage level of this glitch noise is low as compared with the high-voltage transmission signal of about 100V, it is possible to generate an ultrasound image that is not conspicuously influenced by the glitch noise. That is, it is possible to generate an ultrasound image that is not influenced by an artifact resulting from the glitch noise.

On the other hand, in the case of outputting a low-voltage transmission signal, it is possible to inhibit generation of glitch noise resulting from the operation of turning on/off a bias current because the supply of the bias current is continued without turning on/off the bias current. Since the voltage level of the glitch noise reaches a level that cannot be ignored when a low-voltage transmission signal is to be outputted, it is possible, by keeping supplying a bias current, to inhibit generation of the glitch noise. For example, in the contrast imaging mode of administering an ultrasound contrast agent into the subject body and imaging without destroying the ultrasound contrast agent, imaging is performed by outputting a low-voltage transmission signal.

In this embodiment, since generation of glitch noise resulting from the operation of turning on/off a bias current can be inhibited, it is possible to suppress generation of an artifact and perform sensitive harmonic imaging.

Thus, according to the ultrasound imaging apparatus of this embodiment, in the case of outputting a high-voltage transmission signal, it is possible to suppress the power consumption of the transmission circuit and generate an ultrasound image that is not conspicuously influenced by glitch noise. On the contrary, in the case of outputting a low-voltage transmission signal, it is possible, by inhibiting generation of glitch noise, to generate an ultrasound image in which generation of an artifact is inhibited.

Figure 1:
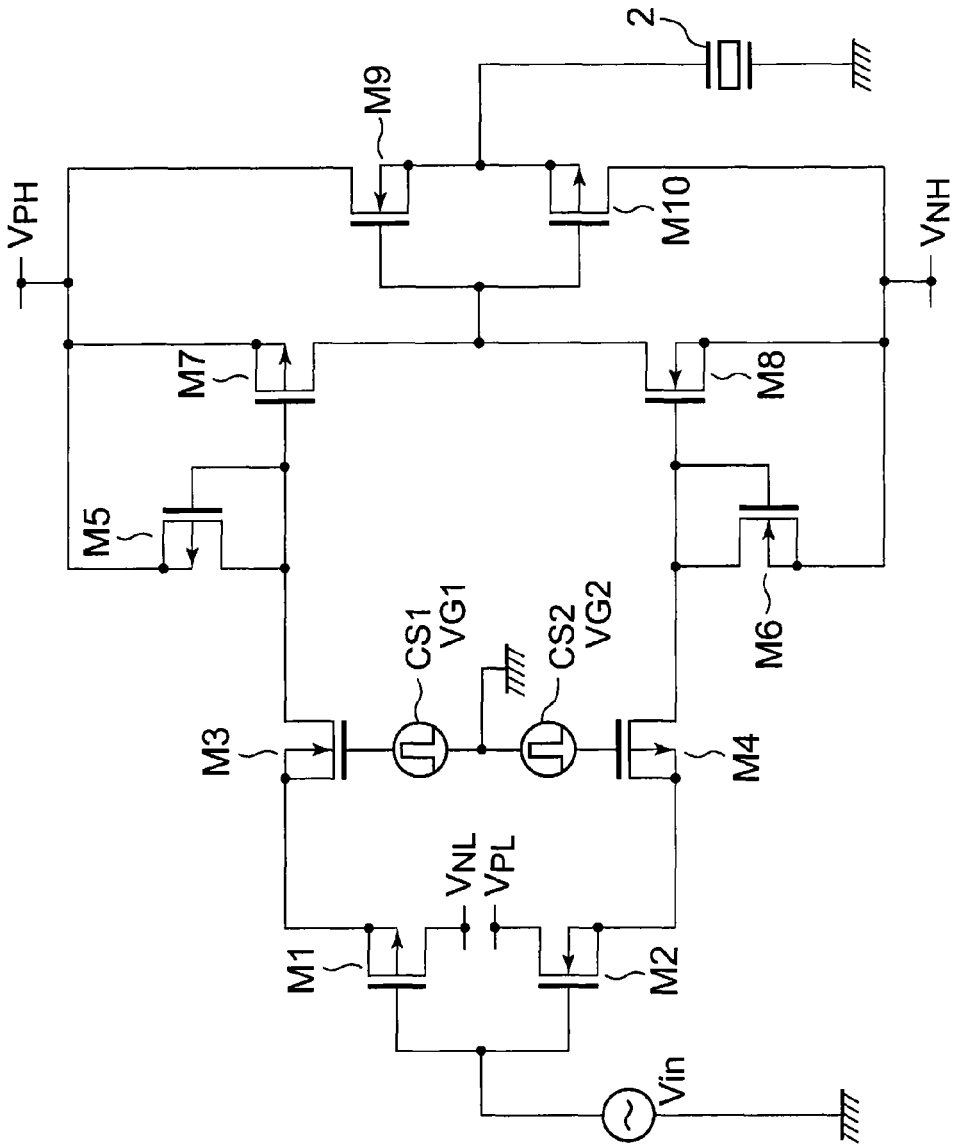
FIG. 1 is a block diagram showing a transmission circuit.
Figure 2:
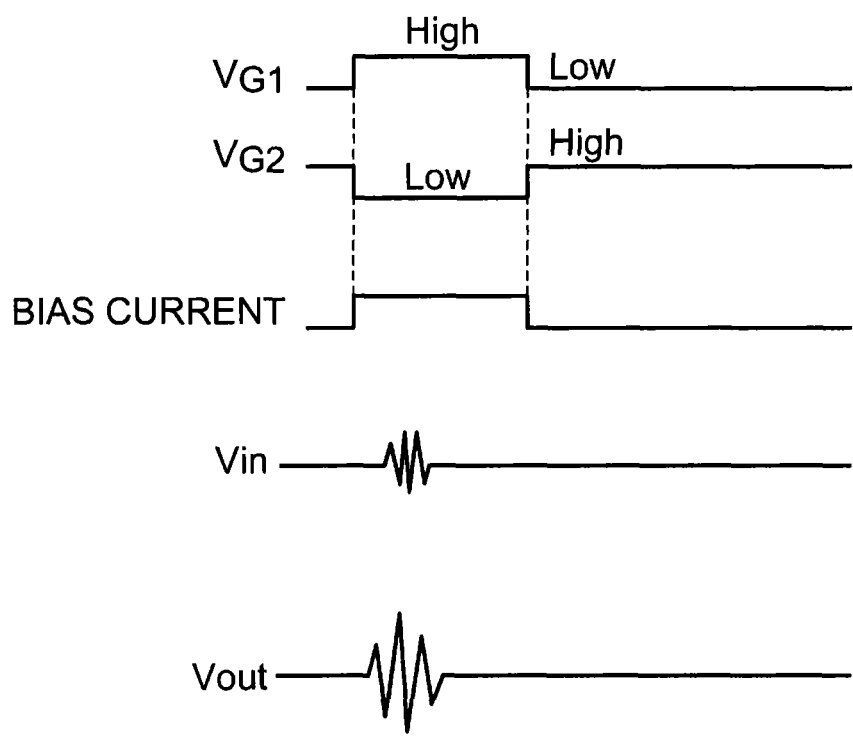
FIG. 2 is a timing chart showing an operation sequence of a transmission circuit of a conventional art.
Figure 3:
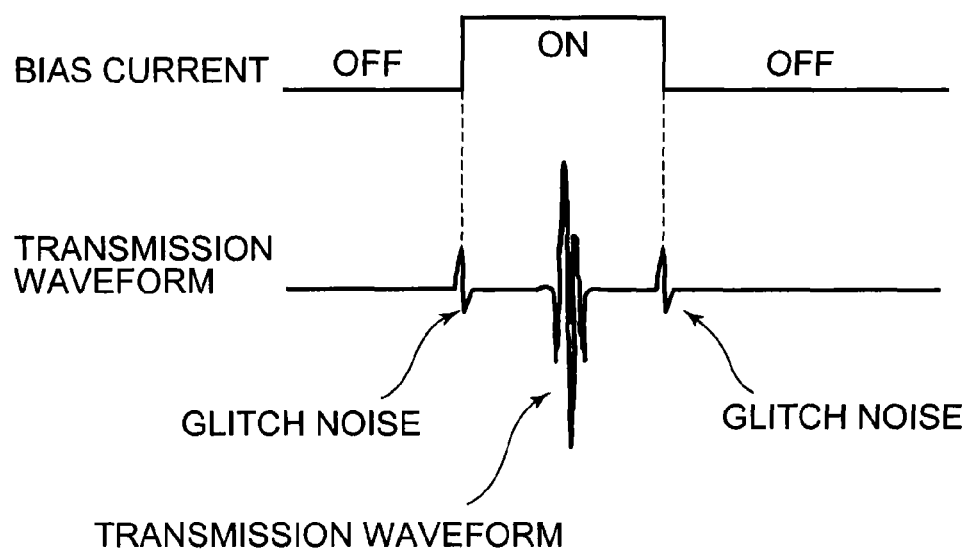
FIG. 3 is a view for describing a generation status of glitch noise generated by turning on/off a bias current when the transmission circuit of the conventional art is operated.
Figure 6:
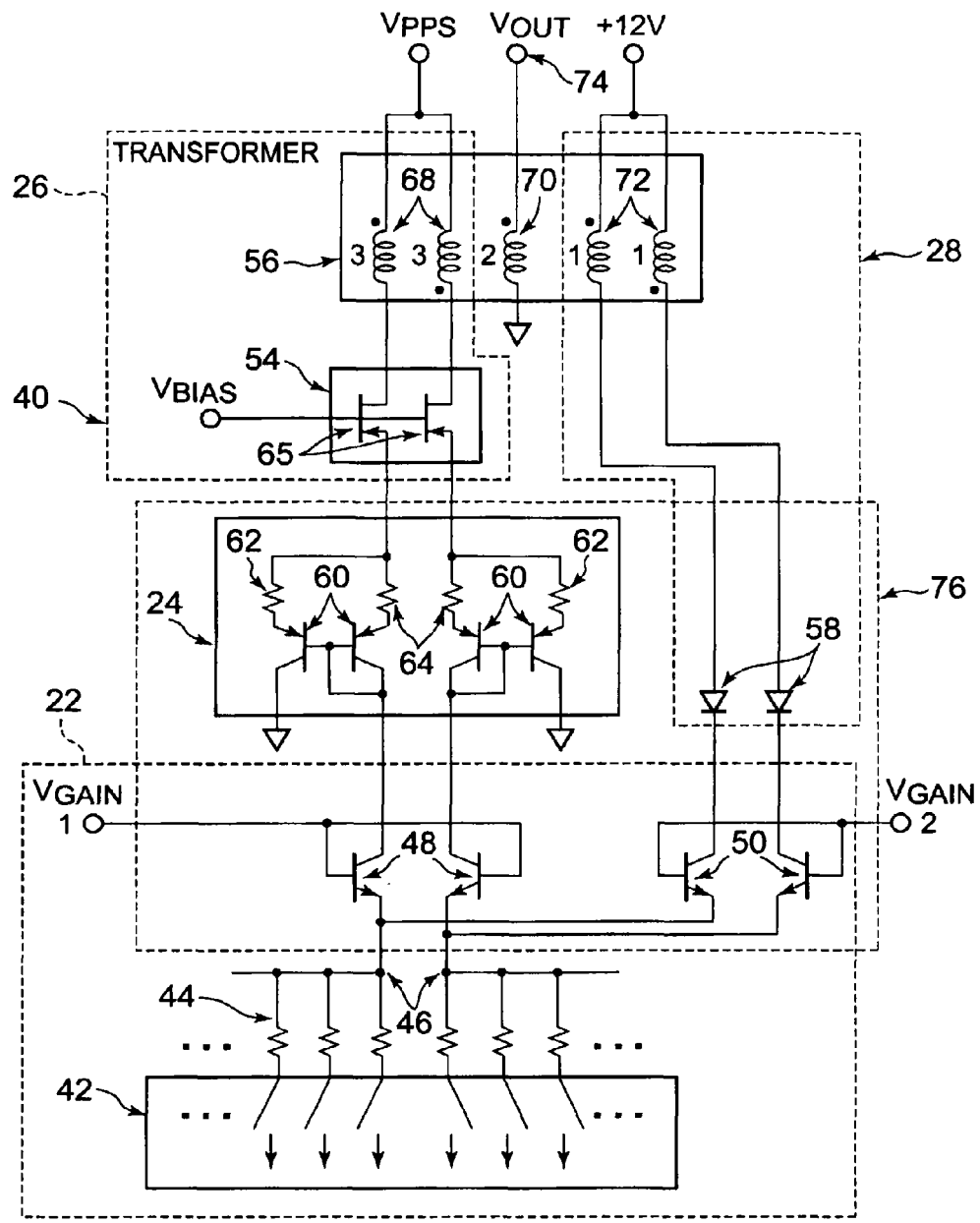
FIG. 6 is a block diagram showing a transmission circuit.

The bias gate part 7 and the transmission pulse generator 10 may be configured by a transmission circuit other than the transmission circuit shown in FIG. 1. For example, the bias gate part 7 and the transmission pulse generator 10 may be configured by a current output type of transmission circuit disclosed in U.S. Pat. No. 6,028,484. The transmission circuit disclosed in U.S. Pat. No. 6,028,484 is shown in FIG. 6. This transmission circuit will be briefly described.

The transmission circuit shown in FIG. 6 includes a transmission signal generation circuit 22, a current amplifier 24, a high voltage amplifier 26, and a low voltage amplifier 28. In the transmission circuit shown in FIG. 6, the current amplifier 24 and the high voltage amplifier 26 are used in the Pulse-Doppler Method (PW method). The low voltage amplifier 28 is used in the Continuous Wave Doppler Method (CW method).

A switch array 42 is connected to a transistor 48 and a transistor 50 via a plurality of resistors 44. In the Pulse-Doppler Method, the current amplifier 24, an output stage 54, and part of a transformer 56 are used. The output stage 54 and the part of the transformer 56 configure the high voltage amplifier 26. On the other hand, in the Continuous Wave Doppler Method, a diode 58 and part of the transformer 56 are used.

In the Pulse-Doppler Method, the gain voltage of the transistor 50 is set to zero, the gain voltage of the transistor 48 is set to several volts, and a current is supplied to the transistor 48. On the other hand, in the Continuous Wave Doppler Method, the gain voltage of the transistor 48 is set to zero, and the gain voltage of the transistor 50 is set to several volts.

The current amplifier 24 is configured by a transistor 60 and a resistor 62. In the Pulse-Doppler Method, the current of a transmission signal is amplified by the current amplifier 24. An output from the current amplifier 24 is supplied to the output stage 54. The output stage 54 is configured by, for example, two transistors 66. A bias voltage $V_{BIAS}$ is supplied to the transistors 66.

The transmission signal outputted from the output stage 54 is supplied to the transformer 56. The transformer 56 is configured by a coil 68 for the Pulse-Doppler Method, a coil 70 for output, and a coil 72 for the Continuous Wave Doppler Method. The transmission signal outputted from the transformer 56 is supplied from an output part 74 to the array transducer elements 2.

In the current output type of transmission circuit shown in FIG. 6, the number of selection switches of the switch array 42 is selected, and a transmission signal is converted to an analog signal, amplified, and outputted as a high-voltage transmission signal. The sum of currents flown from the switch array 42 is amplified at the gain voltage $V_{GAIN}$ and outputted as an output $V_{out}$ via the transformer 56. In the case of the current output type of transmission circuit, it is possible, by using a part for switching the gain voltage $V_{GAIN}$ or a current made to flow to the switch array 42 as the bias gate, to make the transmission circuit operate in a similar manner as the transmission circuit shown in FIG. 1.

The bias gate part 7 may change the value of a bias current depending on the frequency and amplitude of a transmission signal. The transmission circuit is configured by a transistor such as an FET (Field Effect Transistor), whose response characteristic is different depending on the frequency and amplitude of a transmission signal. When a bias current is too small, the distortion of a transmission signal becomes large and the frequency response becomes slow, with the result that it is impossible to follow a high-frequency pulse.

In this embodiment, by changing the value of a bias current in accordance with the frequency and amplitude of a transmission signal, it is possible to inhibit the power consumption of the transmission circuit.

In a case that the frequency of a transmission signal is low, it is possible to generate and output a high-voltage transmission signal without distortion even if the value of a bias current is small. In this embodiment, the transmission mode controller 5 decreases the value of a bias current as the frequency of a transmission signal lowers. The bias gate part 7 supplies a bias current to the transmission pulse generator 10 in accordance with the current value determined by the transmission mode controller 5. Thus, in a case that the frequency of a transmission signal is low, it is possible to inhibit the power consumption of the transmission circuit by making the value of a bias current supplied to the transmission pulse generator 10 small.

For example, the threshold value of the frequency may be previously set in the transmission mode controller 5 so that the transmission mode controller 5 determines the value of a bias current in accordance with the threshold value. To be specific, a first bias current value and a second bias current value, which is smaller than the first bias current value, are previously set in the transmission mode controller 5. In a case that a transmission signal having a frequency less than the threshold value is to be outputted, the transmission mode controller 5 outputs information representing the smaller second bias current value to the bias gate part 7. The bias gate part 7 supplies a second bias current that is small in value to the transmission pulse generator 10.

Further, the transmission mode controller 5 may change the value of a bias current in stages in accordance with the level of the frequency of a transmission signal. For example, in accordance with the level of the frequency of a transmission signal, a plurality of bias current values are previously set in the transmission mode controller 5.

The transmission mode controller 5 determines a bias current value corresponding to the level of the frequency of a transmission signal, and outputs information representing the bias current value to the bias gate part 7. Consequently, the bias gate part 7 supplies a bias current of the value corresponding to the level of the frequency of the transmission signal to the transmission pulse generator 10.

In a case that a high-frequency transmission signal and a low-frequency transmission signal are alternately transmitted, the bias current value can be decreased at the time of transmission of the low-frequency transmission signal, and the bias current value can be increased at the time of transmission of the high-frequency transmission signal.

Further, in the case of outputting a low-voltage transmission signal, it is possible to amplify the input voltage Vin to a required voltage without supplying the same bias voltage as in the case of the high-voltage transmission signal. In this embodiment, the transmission mode controller 5 decreases a bias current value as the voltage of a transmission signal decreases. The bias gate part 7 supplies a bias current to the transmission pulse generator 10 in accordance with the value determined by the transmission mode controller 5. Consequently, in the case of outputting a low-voltage transmission signal, by making a bias current supplied to the transmission pulse generator 10 small, it is possible to inhibit the power consumption of the transmission circuit.

For example, the threshold value of the voltage may be previously set in the transmission mode controller 5 so that the transmission mode controller 5 determines a bias current value in accordance with the threshold value. To be specific, a first bias current value and a second bias current value, which is smaller than the first bias current value, are set in the transmission mode controller 5. In a case that a transmission signal having a voltage less than the threshold value is to be outputted, the transmission mode controller 5 outputs information representing the smaller second bias current value to the bias gate part 7. The bias gate part 7 supplies a second bias current that is small in value to the transmission pulse generator 10.

The transmission mode controller 5 may change the bias current value in stages in accordance with the level of the voltage of a transmission signal. For example, a plurality of bias current values are previously set in the transmission mode controller 5 in accordance with the voltage levels of transmission signals. The transmission mode controller 5 determines the bias current value corresponding to the level of the voltage of a transmission signal and outputs information representing the bias current value to the bias gate part 7. Consequently, the bias gate part 7 supplies a bias current of the value corresponding to the level of the voltage of the transmission signal to the transmission pulse generator 10.

In a case that a high-voltage transmission signal and a low-voltage transmission signal are alternately transmitted, the bias current value can be decreased at the time of transmission of the low-voltage transmission signal, and the bias current value can be increased at the time of transmission of the high-voltage transmission signal. Alternatively, the bias current value may be changed in accordance with the frequency and voltage of a transmission signal.

What is claimed is:

1. An ultrasound imaging apparatus, comprising:
   a plurality of transducers;
   a part configured to receive a synchronizing signal indicating a period for transmitting and receiving ultrasound waves and output a transmission signal after a first time t1 from a time indicated by the synchronizing signal;
   a bias current supply part configured to receive the synchronizing signal and, in a case that an output voltage supplied to the plurality of transducers is equal to or more than a threshold value, supply a bias current during a time interval ΔT2 including a time interval ΔT1 during which the transmission signal is outputted, before a time point that the first time t1 elapses and after a lapse of a second time t2 shorter than the first time t1 from the time indicated by the synchronizing signal and, in a case that the output voltage is less than the threshold value, keep supplying the bias current from a time point a third time t3 indicating a time after which the first time t1 is elapsed before the time indicated by a subsequent synchronizing signal;

an amplifier configured to receive the supply of the bias current to amplify the transmission signal to the output voltage and supply the transmission signal to the plurality of transducers; and an image generator configured to generate ultrasound image data based on reception signals received by the plurality of transducers.

2. The ultrasound imaging apparatus according to claim 1, wherein the bias current supply part is configured to change a level of the bias current in accordance with a level of the output voltage and supply the bias current.

3. The ultrasound imaging apparatus according to claim 1, wherein the bias current supply part is configured to change a level of the bias current in accordance with a frequency of the output voltage and supply the bias current.

4. A method for generating an ultrasound image, comprising:

receiving a synchronizing signal indicating a period for transmitting and receiving ultrasound waves, and outputting a transmission signal after a first time t1 from a time indicated by the synchronizing signal;

receiving the synchronizing signal and, in a case that an output voltage supplied to a plurality of transducers is equal to or more than a threshold value, supplying a bias current during a time interval ΔT2 including a time interval ΔT1 during which the transmission signal is outputted, before a time point that the first time t1 elapses and after a lapse of a second time t2 shorter than the first time t1 from the time indicated by the synchronizing signal and, in a case that the output voltage is less than the threshold value, keeping supplying the bias current from a time point a third time t3 indicating a time after the first time t1 is elapsed before the time indicated by a subsequent synchronizing signal;

receiving the supply of the bias current to amplify the transmission signal to the output voltage and supply the transmission signal to the plurality of transducers; and generating ultrasound image data based on reception signals received by the plurality of transducers.

5. The method for generating the ultrasound image according to claim 4, wherein the bias current is supplied after a level thereof is changed in accordance with a level of the output voltage.

6. The method for generating the ultrasound image according to claim 4, wherein the bias current is supplied after a level thereof is changed in accordance with a frequency of the output voltage.

7. The method for generating the ultrasound image according to claim 4, comprising:

turning off the bias current after the time interval ΔT2; and turning the bias current on at the third time point t3.

8. The method for generating the ultrasound image according to claim 7, comprising:

maintaining the bias current on from the time point t3 until after the transmission signal is output at the output voltage lower than the threshold voltage following the subsequent synchronizing signal.

9. The ultrasound imaging apparatus according to claim 1, comprising the bias current supply part being configured to turn off the bias current after the time interval ΔT2 and turn on the bias current at the third time point t3.

10. The ultrasound imaging apparatus according to claim 9, comprising the bias current supply part being configured to maintain the bias current on from the time point t3 until after the transmission signal is output at the output voltage lower than the threshold voltage following the subsequent synchronizing signal.

* * * * *